(12) United States Patent
Causey, III et al.

(10) Patent No.: US 6,752,787 B1
(45) Date of Patent: Jun. 22, 2004

(54) COST-SENSITIVE APPLICATION INFUSION DEVICE

(75) Inventors: James D. Causey, III, Simi Valley, CA (US); William H. Stutz, Jr., Eagle Rock, CA (US); Clyde K. Nason, Valencia, CA (US); Sheldon B. Moberg, Granada Hills, CA (US); Jay Yonemoto, Diamond Bar, CA (US)

(73) Assignee: Medtronic MiniMed, Inc.,, Northridge, CA (US)

( * ) Notice: Subject to any disclaimer, the term of this patent is extended or adjusted under 35 U.S.C. 154(b) by 0 days.

(21) Appl. No.: 09/533,578

(22) Filed: Mar. 23, 2000

Related U.S. Application Data
(60) Provisional application No. 60/138,071, filed on Jun. 8, 1999.

(51) Int. Cl.[7] .............................................. A61M 37/00
(52) U.S. Cl. ........................ 604/131; 604/151; 604/65; 604/67; 604/152; 604/154
(58) Field of Search ................................. 604/131, 151, 604/65, 67, 154, 152; 222/160, 165, 164

(56) References Cited

U.S. PATENT DOCUMENTS

| | | | | |
|---|---|---|---|---|
| 3,498,228 A | * | 3/1970 | Blumle et al. ................. 103/25 |
| 3,886,938 A | * | 6/1975 | Szabo et al. ................. 128/218 |
| 3,895,631 A | * | 7/1975 | Buckles et al. ............. 128/214 |
| 4,210,138 A | * | 7/1980 | Jess et al. ................ 128/214 E |
| 4,231,366 A | * | 11/1980 | Schael ......................... 128/214 |
| 4,269,185 A | * | 5/1981 | Whitney et al. .......... 128/214 F |
| 4,270,532 A | * | 6/1981 | Franetzki et al. ........ 128/213 R |
| 4,373,527 A | * | 2/1983 | Fischell ....................... 128/260 |
| 4,498,843 A | * | 2/1985 | Schneider et al. ............. 417/22 |
| 4,529,401 A | | 7/1985 | Leslie et al. ................. 604/131 |
| 4,543,955 A | * | 10/1985 | Schroeppel ................. 128/635 |
| 5,373,852 A | * | 12/1994 | Harrison et al. ............. 128/733 |
| 4,373,527 A | * | 6/1995 | Fischell .................... 604/891.1 |
| 5,429,602 A | * | 7/1995 | Hauser .......................... 604/65 |
| 5,485,408 A | * | 1/1996 | Blomquist ................... 364/578 |
| 5,658,250 A | * | 8/1997 | Blomquist et al. ............. 604/65 |
| 5,681,285 A | | 10/1997 | Ford et al. ................... 604/151 |
| 5,741,313 A | * | 4/1998 | Davis et al. .................. 607/36 |
| 5,744,793 A | * | 4/1998 | Skell et al. ............... 250/222.1 |
| 5,755,692 A | | 5/1998 | Manicom ..................... 604/152 |
| 5,788,669 A | * | 8/1998 | Peterson ...................... 604/65 |

(List continued on next page.)

FOREIGN PATENT DOCUMENTS

| | | | |
|---|---|---|---|
| CH | 665955 | 12/1978 | ........... A61M/5/00 |
| EP | 0499903 | 2/1992 | ......... A61M/5/172 |
| EP | 0575256 | 6/1993 | .......... G05B/19/12 |
| WO | 9407186 | 3/1994 | .......... G06B/19/12 |
| WO | 9614893 | 5/1996 | ......... A61M/5/145 |

OTHER PUBLICATIONS

International Search Report for International Application No. PCT/US01/09139.

Database WPI, Section Ch, Week 199843, Derwent Publications Ltd., London, GB; Class B07, AN 1998–505404, XP002144981 (Patent Solutions Inc) abstract, & US 5 803 712 A (Davis Davis L et al) Sep. 8, 1998.

*Primary Examiner*—Henry Bennett
*Assistant Examiner*—Camtu Nguyen
(74) *Attorney, Agent, or Firm*—Medtronic MiniMed, Inc.

(57) ABSTRACT

A reusable external infusion device infuses a fluid into an individual's body. The infusion device controls the rate that fluid flows from a reservoir inside a housing, through an external tube, and into the individual's body. Essentially, the infused fluid is insulin. However, many other fluids may be administered through infusion such as, HIV drugs, drugs to treat pulmonary hypertension, iron chelation drugs, pain medications, anti-cancer treatments, vitamins, hormones, and others.

9 Claims, 17 Drawing Sheets

U.S. PATENT DOCUMENTS

| | | | | |
|---|---|---|---|---|
| 5,797,519 A | * | 8/1998 | Schroeder et al. | 222/129.2 |
| 5,895,371 A | | 4/1999 | Levitas et al. | 604/49 |
| 5,960,085 A | * | 9/1999 | de la Huerga | |
| 5,984,894 A | | 11/1999 | Poulsen et al. | 604/151 |
| 6,026,325 A | * | 2/2000 | Weinberg et al. | 607/36 |
| 6,051,887 A | * | 4/2000 | Hubbard | 257/777 |
| RE36,871 E | * | 9/2000 | Epstein et al. | 604/67 |
| 6,142,343 A | * | 11/2000 | Wade et al. | 222/182 |
| 6,375,638 B2 | * | 4/2002 | Nason et al. | 604/132 |

* cited by examiner

COST-SENSITIVE APPLICATION INFUSION DEVICE

RELATED APPLICATIONS

This application claims priority on U.S. Provisional Patent Application Serial No. 60/138,071, filed on Jun. 8, 1999, and entitled "Cost Sensitive Application Infusion Pump", which is specifically incorporated by reference herein.

FIELD OF THE INVENTION

This invention relates to external infusion devices and, in particular embodiments to external infusion devices that control the rate that a fluid is infused into an individual's body.

BACKGROUND OF THE INVENTION

Portable personal infusion devices and systems are relatively well-known in the medical arts, for use in delivering or dispensing a prescribed medication to a patient. Many pharmaceutical agents are delivered into the subcutaneous tissue and the most common is insulin. Currently, more than 70,000 patients in the U.S. and 30,000 more patients worldwide use continuous subcutaneous infusion of insulin (CSII) for the treatment of diabetes mellitus. However, other medications that are infused include HIV drugs, drugs to treat pulmonary hypertension, iron chelation drugs, pain medications, and anti-cancer treatments.

Traditionally, low cost infusion devices have used an elastomeric diaphragm, sponge rubber, balloon or gas generator to expel fluid to be infused into a patient over a period of time at a single, relatively constant rate. A drawback to these devices is that they are only filled with fluid once. When the infusion of fluid is complete, the infusion device is disposed of. Thus, the infusion device must be made at an extremely low cost. Another drawback is that the low cost may not allow for the high quality needed to have sufficient flow rate control accuracy for the delivery of dosage sensitive drugs.

To obviate these drawbacks, infusion devices have been designed with more accurate dosage control, but at a significantly higher cost. To compensate for the relatively high cost, the more accurate infusion devices are designed to be refilled and reused.

In one form, refillable infusion devices comprise a relatively compact housing adapted to receive a syringe or reservoir carrying a prescribed medication for administration to the patient through infusion tubing and an associated catheter or infusion set. Such infusion devices are utilized to administer insulin and other medications, with exemplary infusion device constructions being shown and described in U.S. Pat. Nos. 4,562,751; 4,678,408; 4,685,903; 5,080,653 and 5,097,122, which are incorporated by reference herein.

While the sophisticated electronics and robust mechanics of the more expensive refillable infusion devices provide a more reliable and accurate infusion device, the cost of manufacturing may make the refillable infusion device too expensive for some users or medications. On the other hand, the low cost, one-time-use, constant flow rate infusion devices may not have sufficient flow rate accuracy or the adjustments needed to control the dosage for some users.

SUMMARY OF THE DISCLOSURE

According to an embodiment of the invention, a reusable external infusion device with a predetermined usage life for infusing a fluid into a body includes a replaceable reservoir, a power supply, a drive system, an electronics system, and a housing. The housing contains the reservoir, power supply, drive system and electronics system. The replaceable reservoir contains the fluid before infusing and has a usage life substantially shorter than the predetermined usage life of the infusion device. The power supply provides power to the drive system and the electronics system to force fluid from the reservoir. The electronics system regulates the power from the power supply to control the drive system.

In particular embodiments of the present invention, the infusion device includes a control system operatively coupled to the electronics system that adjusts one or more control parameters. In more particular embodiments, the control system is a supplemental device. In additional embodiments, the supplemental device establishes two way communication with the electronics system. In particular embodiments, the supplemental device has a display.

In preferred embodiments, after the infusion device's predetermined usage life has expired, the infusion device may be refurbished at least once to function for another predetermined usage life. In particular embodiments, when the predetermined usage life for the infusion device expires, the infusion device ceases to infuse fluid. In further particular embodiments, the predetermined usage life for the infusion device is programmed into a software program as a number of times that the replaceable reservoir is replaced in the infusion device.

In preferred embodiments, the drive mechanism of the infusion device contains a DC motor in the drive system. In alternative embodiments, the drive mechanism of the infusion device contains a stepper motor, solenoid motor, a shape memory alloy driven motor, or the like.

According to another embodiment of the present invention, a reusable external infusion device is for infusing a fluid into an individual. In preferred embodiments, the infusion device includes a housing and a replaceable fluid containing reservoir that is inserted into the housing. In preferred embodiments, the housing contains only one electronics module to control the infusion device. In particular embodiments, the electronics module contained within the housing is produced using chip-on-board construction. In other particular embodiments, the electronics module contained within the housing is produced using ball grid array construction. In further embodiments, the electronics module a flex circuit to control the infusion device. In preferred embodiments, the housing contains a detection device that detects the presence or absence of the replaceable reservoir. In further preferred embodiments, the reusable external infusion device further includes a drive mechanism coupled to an electronics system and the housing includes a button coupled to the electronics system that an individual may push to cause the drive mechanism to deliver a bolus of fluid into the individual.

In additional preferred embodiments, the housing and internal contents are assembled together without screws. In more preferred embodiments, the housing includes at least one feature that is fused using ultrasonic vibrations. In other preferred embodiments, the housing includes a drive mechanism that contains at least one non-metallic gear.

In preferred embodiments, the housing includes a slidable key that provides access to remove and/or replace the replaceable reservoir inside the housing. In particular embodiments, the housing accepts a key that includes a communication device for communicating with a supplemental device. In alternative embodiments, the housing accepts a tab that includes a communication device for communicating with a supplemental device. In further alternative embodiments, the housing accepts a tab/key that includes a communication device for communicating with a supplemental device.

In further preferred embodiments, the housing includes an opening to insert a removable tab that includes a programmable chip that contains at least one control parameter to control the infusion device. In further embodiments, the housing includes an opening to insert a tab that includes at least one electrical terminal that establishes electrical contact between at least one set of electrical terminals inside the housing. In particular embodiments, the housing is adapted to receive at least one of at least two different tabs that are insertable into the housing, and the at least two different tabs each have different electrical terminal configurations that establish electrical contact between different electrical terminals inside the housing, and connects different electrical terminals to cause the external infusion device to dispense fluid at different rates. In still further embodiments, the housing is adapted to receive at least one tab with an optically readable pattern, and the housing includes an optical reader to read the optically readable pattern on the at least one tab to control at least one control parameter of the reusable external infusion device. In alternative embodiments, the housing is adapted to receive at least one tab that includes magnetically stored information, and the housing includes a magnetic reader to read the magnetically stored information from the at least one tab to control at least one control parameter of the reusable external infusion device.

In preferred embodiments, the reusable external infusion device includes at least one lithium magnesium oxide ($LiMnO_2$) battery. In particular embodiments, the reusable external infusion device includes a battery that lasts at least 10 weeks, measured while the reusable external infusion device dispenses up to 40 milliliters of fluid per day and while the alarms draw substantially no power from at least one battery.

In additional particular embodiments, an alarm is activated when the reusable external infusion device needs to be refurbished. In preferred embodiments, the reusable external infusion device has a predetermined usage life and when the predetermined usage life has expired, the reusable external infusion device may be refurbished at least once to function for another predetermined usage life. In particular embodiments, the reusable external infusion device has a predetermined usage life and when the predetermined usage life expires, the reusable external infusion device ceases to infuse fluid.

In further particular embodiments, the reusable external infusion device has a predetermined usage life and the predetermined usage life for the reusable external infusion device is programmed into a software program as a number of times that the replaceable reservoir is replaced in the housing, as a number of days that the reusable external infusion device is in use, as the number of times the battery is replaced in the reusable external infusion device, and/or as the number of times that a key is removed from the reusable external infusion device. In other embodiments, the reusable external infusion device has a predetermined usage life and the predetermined usage life for the reusable external infusion device is expired when the amount of electrical power consumed to empty a reservoir exceeds a predetermined amount programmed into a software program.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
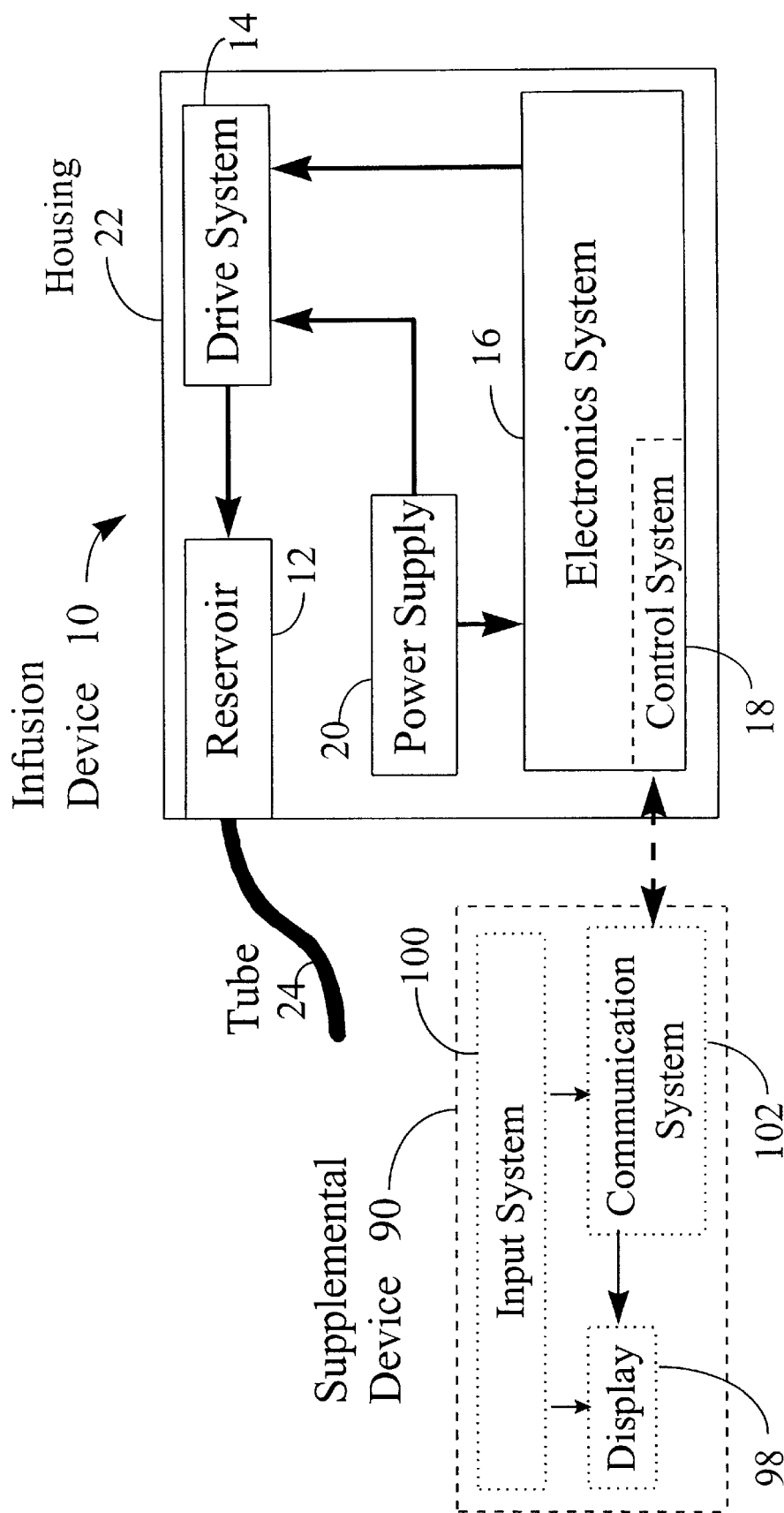
FIG. 1 is a block diagram, illustrating an infusion device and a supplemental device according to an embodiment of the present invention.

As shown in the drawings for purposes of illustration, the invention is embodied in a reusable external infusion device for infusing a fluid into an individual's body and methods of manufacturing the same. The infusion device controls the rate that fluid flows from a reservoir inside a housing, through an external tube, and into the individual's body. In preferred embodiments, the infused fluid is insulin. In alternative embodiments, many other fluids may be administered through infusion such as, but not limited to, HIV drugs, drugs to treat pulmonary hypertension, iron chelation drugs, pain medications, anti-cancer treatments, vitamins, hormones, or the like.

Figure 2:
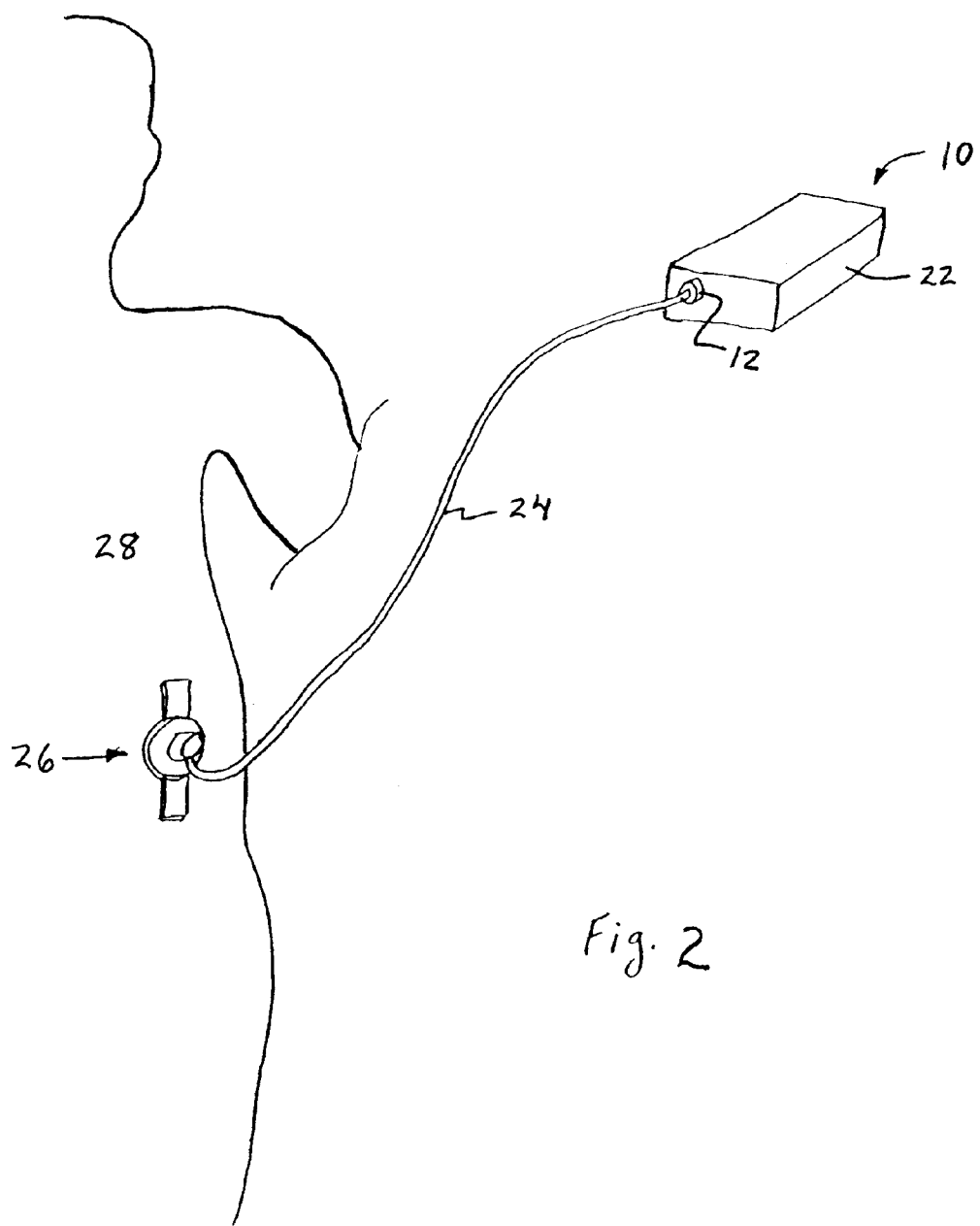
FIG. 2 is a perspective view of an infusion device connected to a tube, an infusion set and an individual's body according to an embodiment of the present invention.
Figure 3:
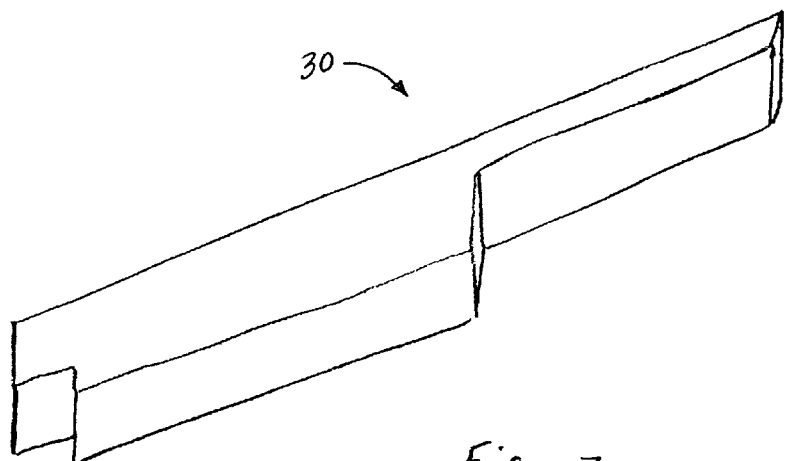
FIG. 3 is a perspective view of an electronics module in accordance with an embodiment of the present invention.

In preferred embodiments, as shown in FIG. 1, an infusion device 10 includes a reservoir 12, a drive system 14, an electronics system 16, a control system 18, and a power supply 20, all contained within a housing 22. The fluid is pushed from the reservoir 12 by the drive system 14 when commanded by the electronics system 16. The power supply 20 provides power to both the drive system 14 and the electronics system 16. A user or another qualified person, such as a doctor, parent, or spouse interfaces with the electronics system 16 through the control system 18. In preferred embodiments, fluid flows from the infusion device 10, through the external tube 24, into an infusion set 26, and then into the individual's body 28, as shown in FIG. 2. Infusion sets 26 that may be used in conjunction with the infusion device 10 are described in, but not limited to, U.S. Pat. Nos.; 4,723,947; 4,755,173; 5,176,662; and 5,584,813; and disclosed in U.S. patent application Ser. No. 09/034,626, filed Mar. 4, 1998 and entitled "Medication Infusion Set", which are hereby incorporated by reference.

The control system 18 provides a method for the user or another qualified person to adjust one or more control parameters that the electronics system 16 uses to calculate and issue commands to the drive system 14. Control parameters include, for example, one or more basal rates, one or more bolus rates, maximum and minimum delivery rates, one or more alarm criteria, or the like.

In preferred embodiments, the electronics system 16 is a compilation of one or more electrical elements designed to carryout commands as specified by the control parameters. Electrical elements may include, but are not limited to, resistors, capacitors, amplifiers, diodes, semiconductor circuits, traces, wires, antennae, buttons, sound emanating devices, light emitting devices, receivers, transmitters, switches, or the like. In preferred embodiments, the electrical elements are attached to a single electronics board to form an electronics module. In particular embodiments, an electronics module 30 is a "popsickle stick" design, as shown in FIGS. 3, 5, 10 and 22. The term "popsickle stick" refers to the electronics module's long thin layout that optimizes the usage of space within the housing 22. With the "popsickle stick" design, the electronics module 30 stretches the length of the housing 22 so that only short leads are needed to extend from the electronics module 30 to any component that uses electricity or signals from the electronics. The use of a "popsickle stick" design also facilitates ease of assembly and integrating for the infusion device 10.

Figure 4:
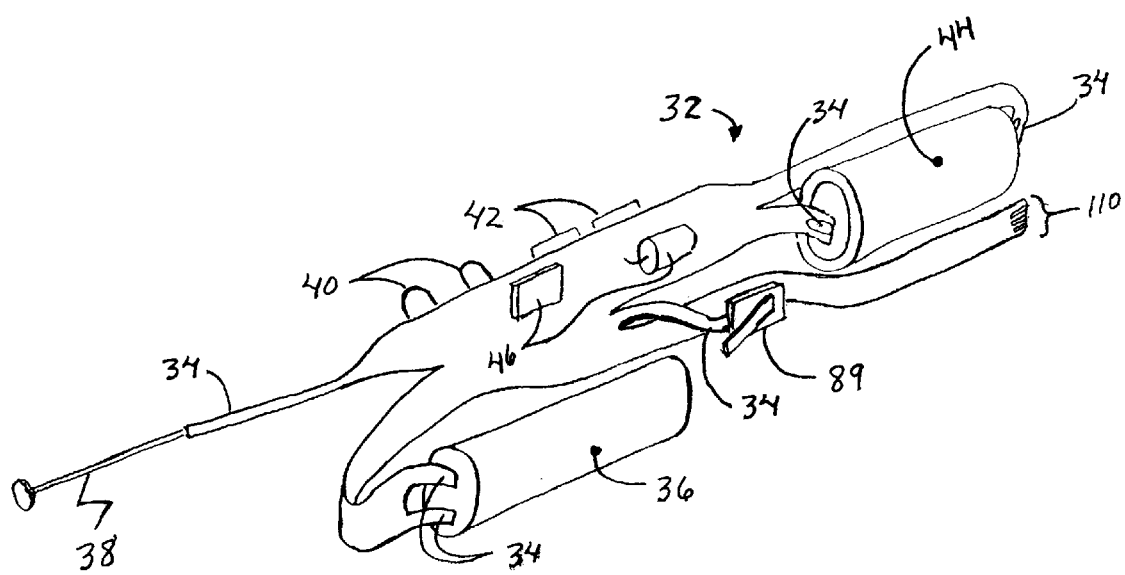
FIG. 4 is a perspective view of a flex circuit in accordance with an embodiment of the present invention.

In alternative embodiments, the electrical elements of the electronics module are mounted on a flex circuit. Preferably, the flex circuit has one or more flex circuit leads 34 that run to various locations within the housing 22 to minimize or eliminate the need for wires. An example of one embodiment of a flex circuit 32 is shown in FIG. 4. Flex circuit leads 34 may run to a motor 36, an antenna 38, one or more LEDs 40, one or more buttons 42, a battery 44, electrical elements 46, or the like. In additional embodiments, the flex circuit 32 may connect to other devices or components such as a transmitter, a receiver, a display, an alarm, a tab, a communication port, a power port, or the like. In additional embodiments, one or more semiconductor circuits are wire bonded to the flex circuit 32.

In preferred embodiments, the electronics module 30 includes chip-on-board construction. In alternative embodiments, the electronics module 30 includes ball grid array (BGA) packages or leaded chip construction.

In preferred embodiments, the electronics system 16 includes one or more LEDs 40 to indicate specific conditions about the infusion device 10, such as whether the fluid is being dispensed, the battery power level, the fluid level in the reservoir 12, whether the electronics system 16 is functioning, warnings regarding how soon the infusion device 10 will require servicing, or the like. In preferred embodiments, the electronics system 16 includes one or more alarms. Preferably, an alarm is a piezo electric sound device. In alternative embodiments, the one or more alarms includes a vibrator, a light, a sound emanating device, or the like.

Figure 5:
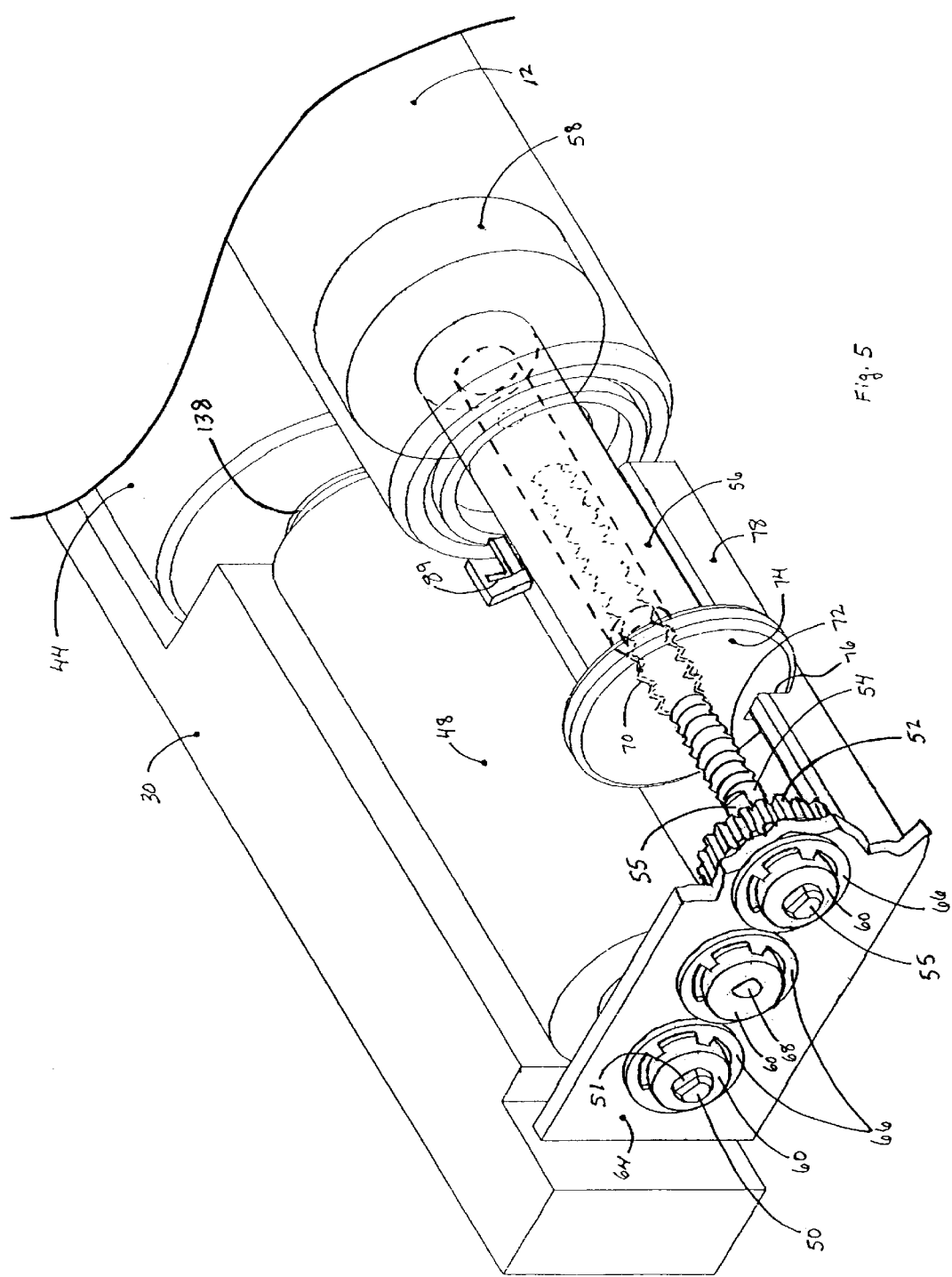
FIG. 5 is a partial perspective view of an infusion device drive system in accordance with an embodiment of the present invention.
Figure 22:
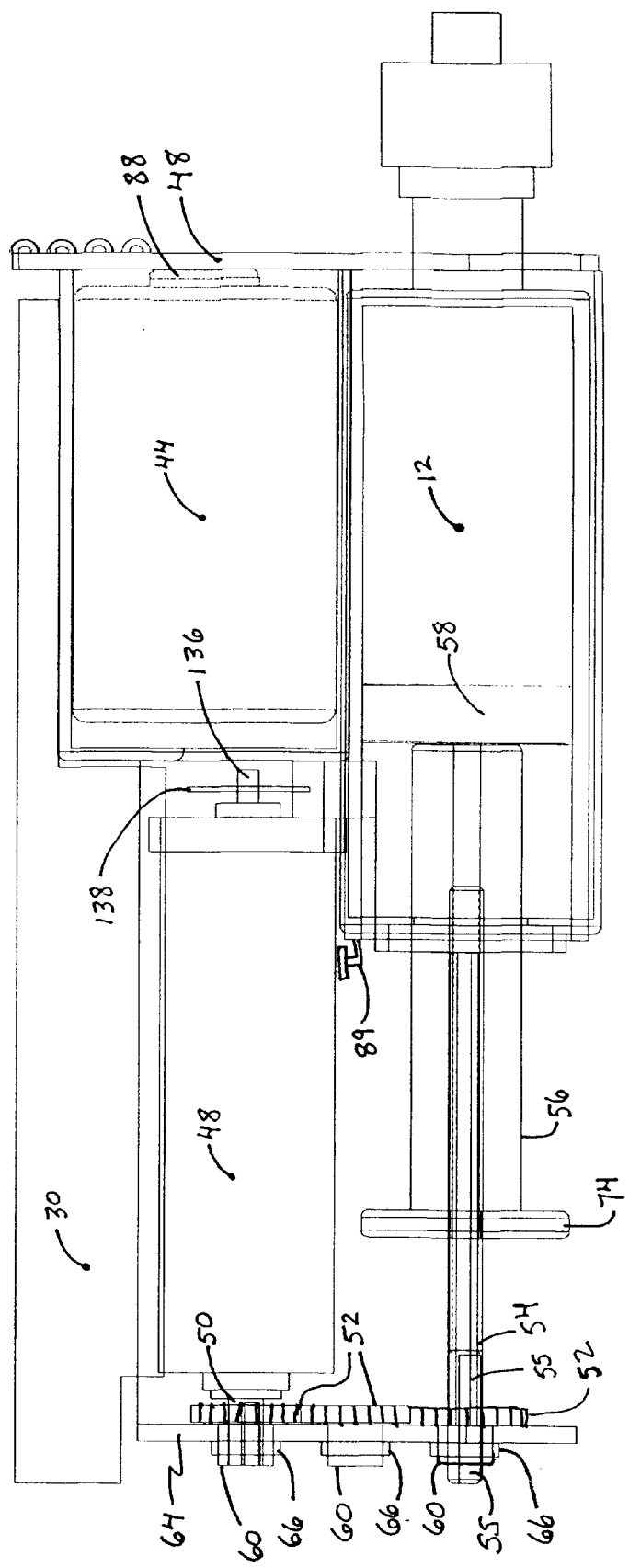
FIG. 22 is a plan view of the internal components of an infusion pump in accordance with an embodiment of the present invention.

In preferred embodiments, as shown in FIGS. 5 and 22, the drive system 14 includes a motor/gear box 48 with a drive shaft 50 that extends out of the motor/gear box 48, one or more gears 52 external to the motor/gear box 48 that transfers motion from the drive shaft 50 to a lead screw 54, and a piston 56 that is coupled to the lead screw 54, such that as the lead screw 54 rotates, the piston 56 moves a plunger 58 inside the reservoir-12. The angular rotation of a motor shaft 136 is measured with an optical encoder 138 attached to an end of a motor shaft 136 protruding from the motor/gear box 48. In other embodiments, the drive system 14 may also be the same as or similar to the drive mechanism described in, U.S. patent application Ser. No. 09/429,352, filed Oct. 28, 1999 and entitled "Compact Pump Drive System", which is hereby incorporated by reference. In particular embodiments, the motor/gear box 48 includes a stepper motor. In alternative embodiments, the motor/gear box 48 uses a direct current (DC) motor, a solenoid motor or a shape memory alloy (SMA) driven motor. The SMA motor may be of the type described in U.S. patent application Ser. No. 09/249,666, filed on Feb. 12, 1999, entitled "Incremental Motion Pump Mechanisms Powered By Shape Memory Alloy Wire Or The Like", which is hereby incorporated by reference. The SMA motor may include a ratchet/pawl mechanism actuated by a SMA component.

In preferred embodiments, the one or more gears 52 external to the motor/gear box 48 have a one-to-one gear ratio. However, in alternative embodiments, the gears may have different gear rations such as 1.5:1, 2:1, 3:1, 5: 1, or the like depending on the motor control resolution and the minimum dosage requirement for the fluid. In particular embodiments, the gears 52 are made of molded plastic. In alternative embodiments, the gears 52 are made of metal, epoxy, laminates, or other suitably strong materials. In alternative embodiments, mechanical power is transferred from the motor/gear box 48 to the lead screw 54 using one or more of a belt, timing belt, chain, gears, rack or the like.

Figure 6:
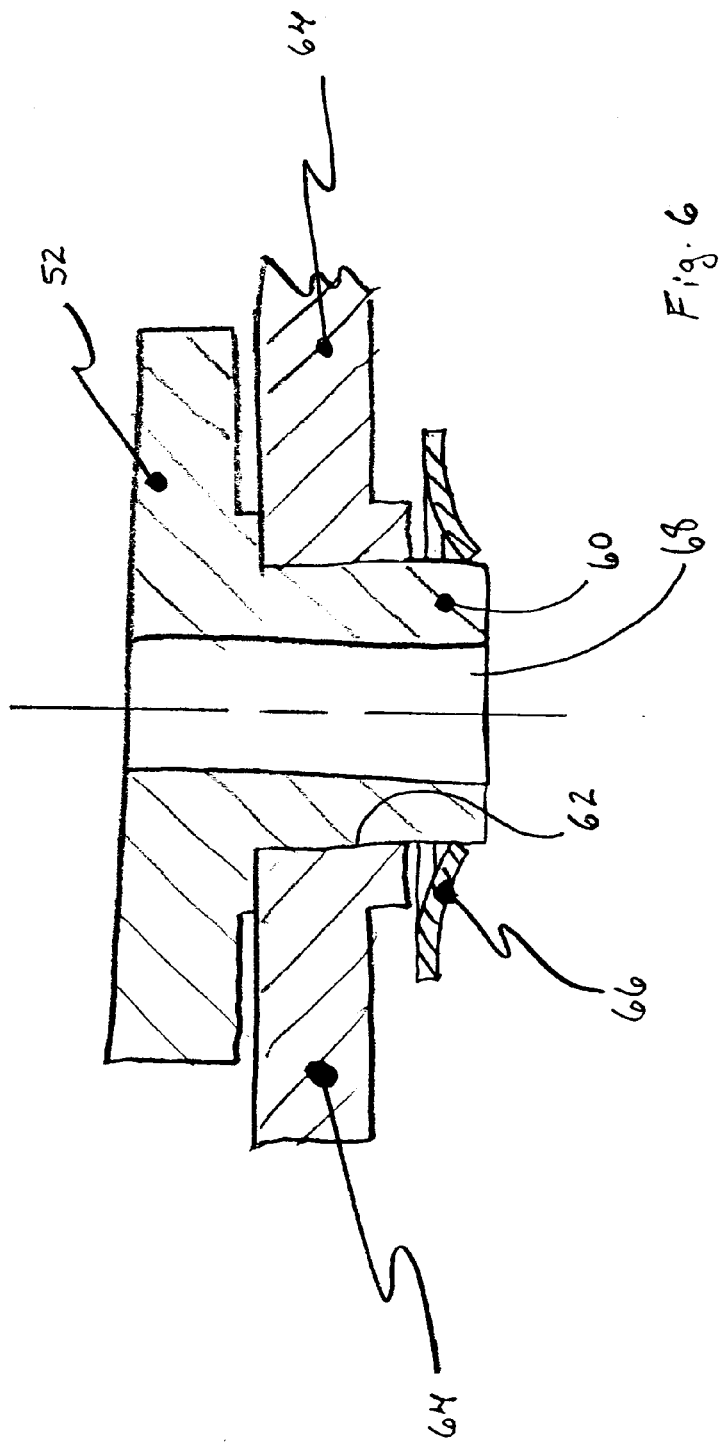
FIG. 6 is a cross-sectional view showing "Tinnerman" style retaining rings holding gear hubs in accordance with an embodiment of the present invention.

As shown on FIG. 6, in preferred embodiments, each of the gears 52 have a gear hub 60 that fits through one of the openings 62 in a wall 64 contained within the housing 22. A "Tinnerman" style retaining ring 66 slips over the gear hub 60 of each gear 52 to secure the gear 52 to the wall 64. In alternative embodiments, each gear hub 60 is held in place with a snap ring, a rivet, a threaded nut, a press-on nut, or the like. In preferred embodiments, each gear 52 has a "D" shaped hole 68 passing entirely through the gear 52 that is located generally at the center of rotation. The drive shaft 50, with a mating "D" shaped end 51, fits into the "D" shaped hole 68 in a gear 52. In addition, a "D" shaped end 55 of the lead screw 54 fits into a "D" shaped hole 68 in a gear 52. The "D" shaped holes 68 function to transmit torque from the drive shaft 50 to the gears 52 and on to the lead screw 54 without the need for a fixed attachment of the drive shaft 50 and the lead screw 54 to the gear hubs 60. In alternative embodiments, other shaped holes are used such as hexagonal, square, rectangular, polygonal, triangular, oval, star, clover, round, notched, or the like along with a drive shaft and a lead screw with mating ends that fit into the holes.

As shown in FIG. 5, in preferred embodiments, the piston 56 has a threaded bore 70 that is generally centered with the piston's longitudinal axis, and the threads 72 on the lead screw 54 mate with the threaded bore 70 on the piston 56. Preferably only the first half of an inch of the piston bore 70 is threaded and the remainder of the bore through the rest of the piston is smooth with a large enough diameter to allow the lead screw to pass through unobstructed. Alternatively, the length of the piston bore that is threaded may be increased or decreased depending on the number of threads needed to apply force to the plunger and the amount of friction generated between the piston bore 70 and the lead screw 54. Preferably, the piston 56 includes a flange 74 with a notch 76 that fits over a rail 78. The rail 78 runs generally parallel to the lead screw 54. As the lead screw 54 rotates, an edge of the notch 76 in the piston flange 74 rests against the rail 78 and prevents the piston 56 from rotating. Therefore, as the lead screw 54 rotates, the piston 56 moves along the length of the lead screw 54 substantially free of rotational movement. In alternative embodiments, the threaded bore 70 in the piston 56 is not generally centered with the piston's centerline. For example, the lead screw 54 may pass through the piston's flange 74.

Figure 7:
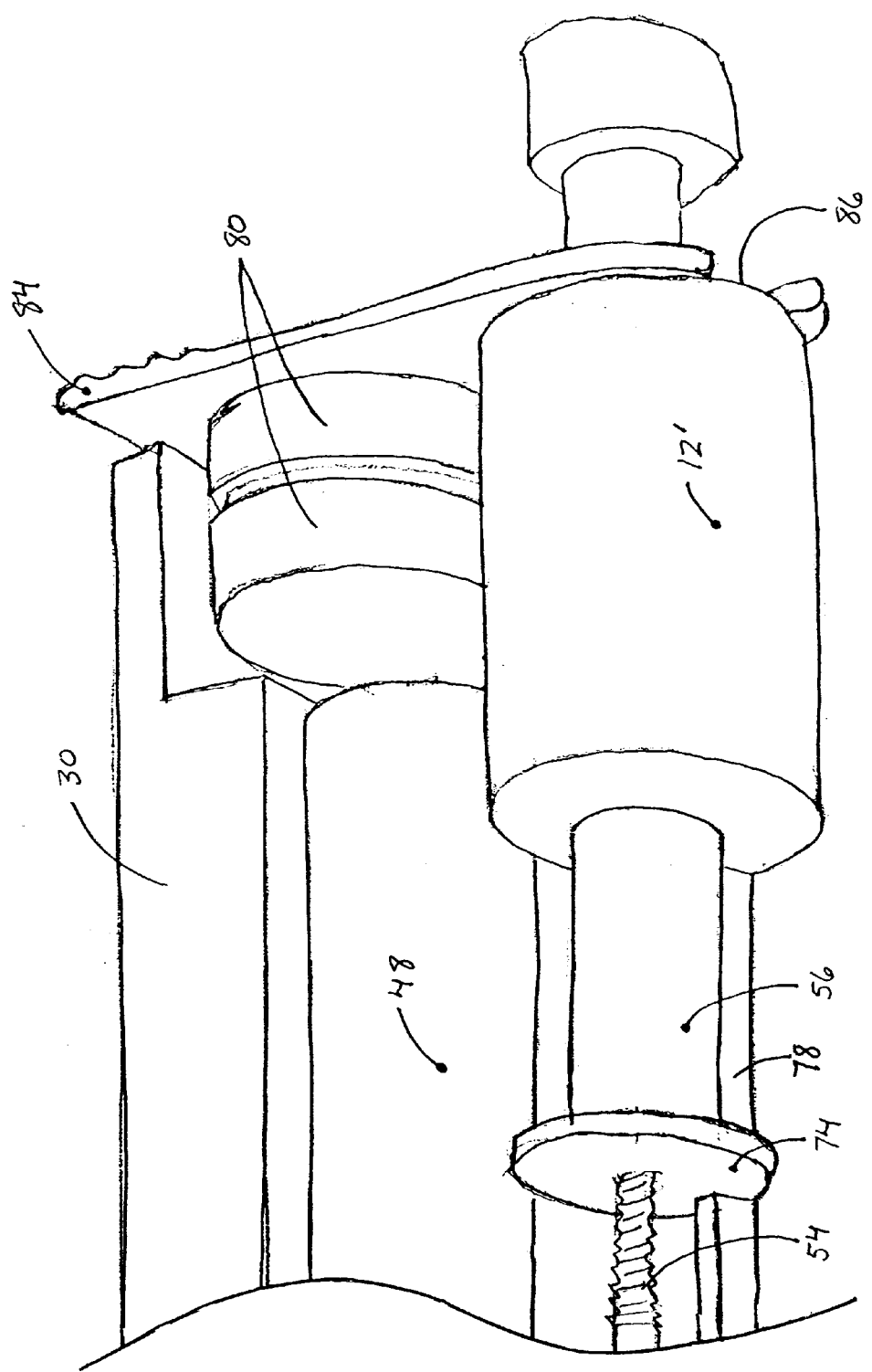
FIG. 7 is a partial perspective view of internal components of an infusion device with multiple batteries in accordance with another embodiment of the present invention.
Figure 10:
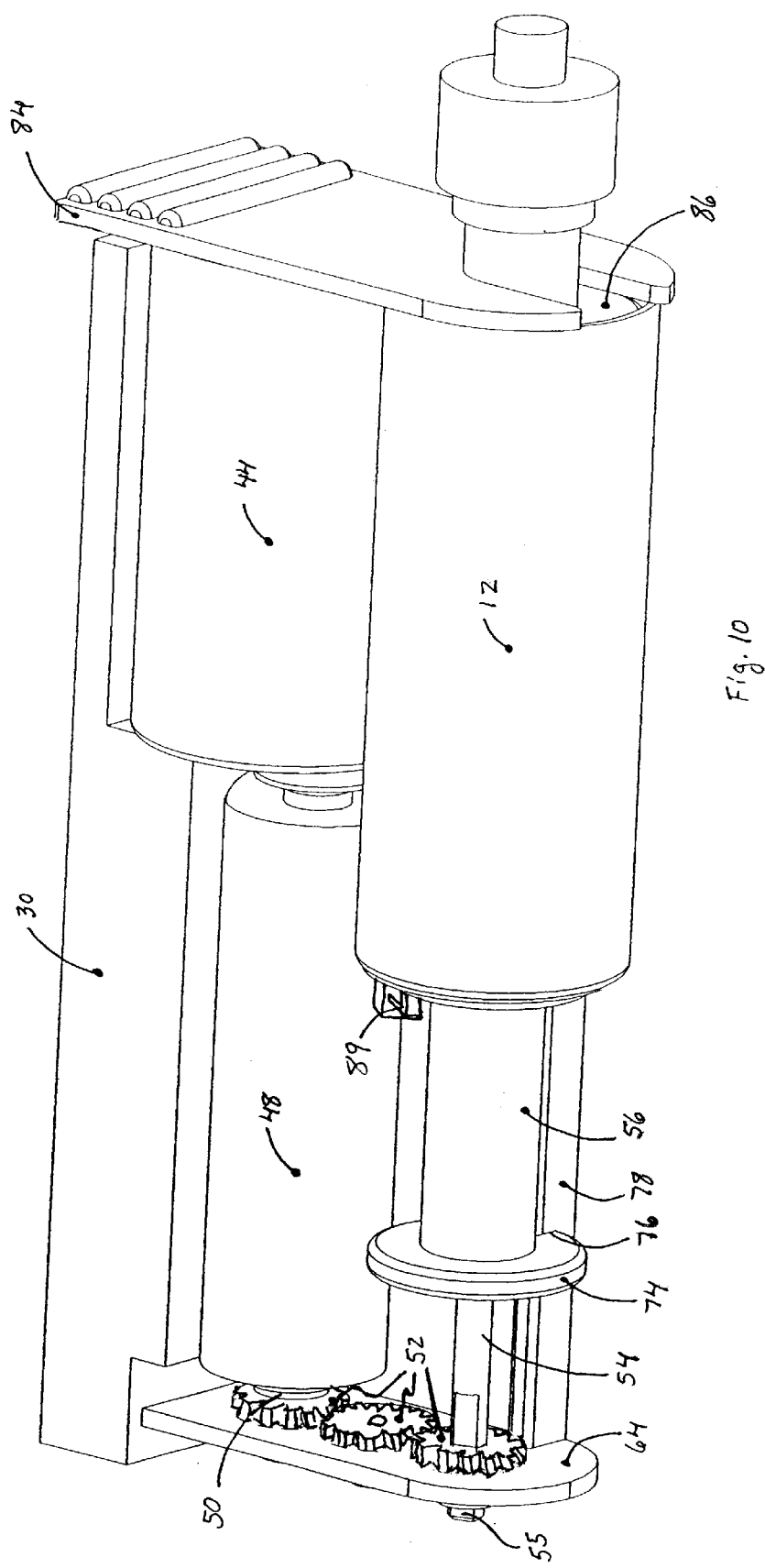
FIG. 10 is a perspective view of the infusion device of FIG. 8 with the housing removed to show the internal components and the key.

In preferred embodiments, the power supply is a battery 44. In particular embodiments, the power supply is a lithium magnesium oxide (Li Mn $O_2$) battery 44, as shown in FIGS. 4, 5 and 10. Some of the factors that influence the size of the battery 44 are, the amount of power needed to drive the motor/gear box 48, the amount of friction through out the drive system 14, the size of the reservoir 12 (and therefore the amount of piston 56 displacement needed to empty the reservoir 12), the dosage resolution required, the dosage volume, whether or not alarms are set off, how frequently lights or displays are used, and the number of days desired between battery 44 replacement. In preferred embodiments, the battery 44 lasts at least 10 weeks, while the reusable infusion device 10 dispenses fluid at a rate of up to 40 milliliters per day without alarms. At greater fluid dispensing rates and/or when the alarms are active, the battery duration may be diminished. In preferred embodiments, with a 3 ml reservoir 12, the battery capacity is generally 2.1 amp-hours at 3 volts. In other embodiments, with a 1.5 ml reservoir 12', such as shown in FIG. 7, the combined capacity of a pair of batteries 80, shown in FIG. 7, is generally 1.1 amp-hours at 3 volts. In alternative embodiments, the battery 44 may last as little as 3 days (a common time to empty a reservoir 12) with a battery capacity as low as 0.035 amp-hours. Or, the battery 44 may last as long as a year (a likely time to have the infusion device 10 serviced) with a better battery capacity as large as 12.6 amp-hours. And in other alternative embodiments, the battery voltage may be as low as 0.5 volts and as large as 9 volts depending on the power needed for the drive system 14 and electronics system 16. In further alternative embodiments, two or more batteries (FIG. 7) may be used to supply the voltage and capacity needed to operate the infusion device 10.

Figure 8:
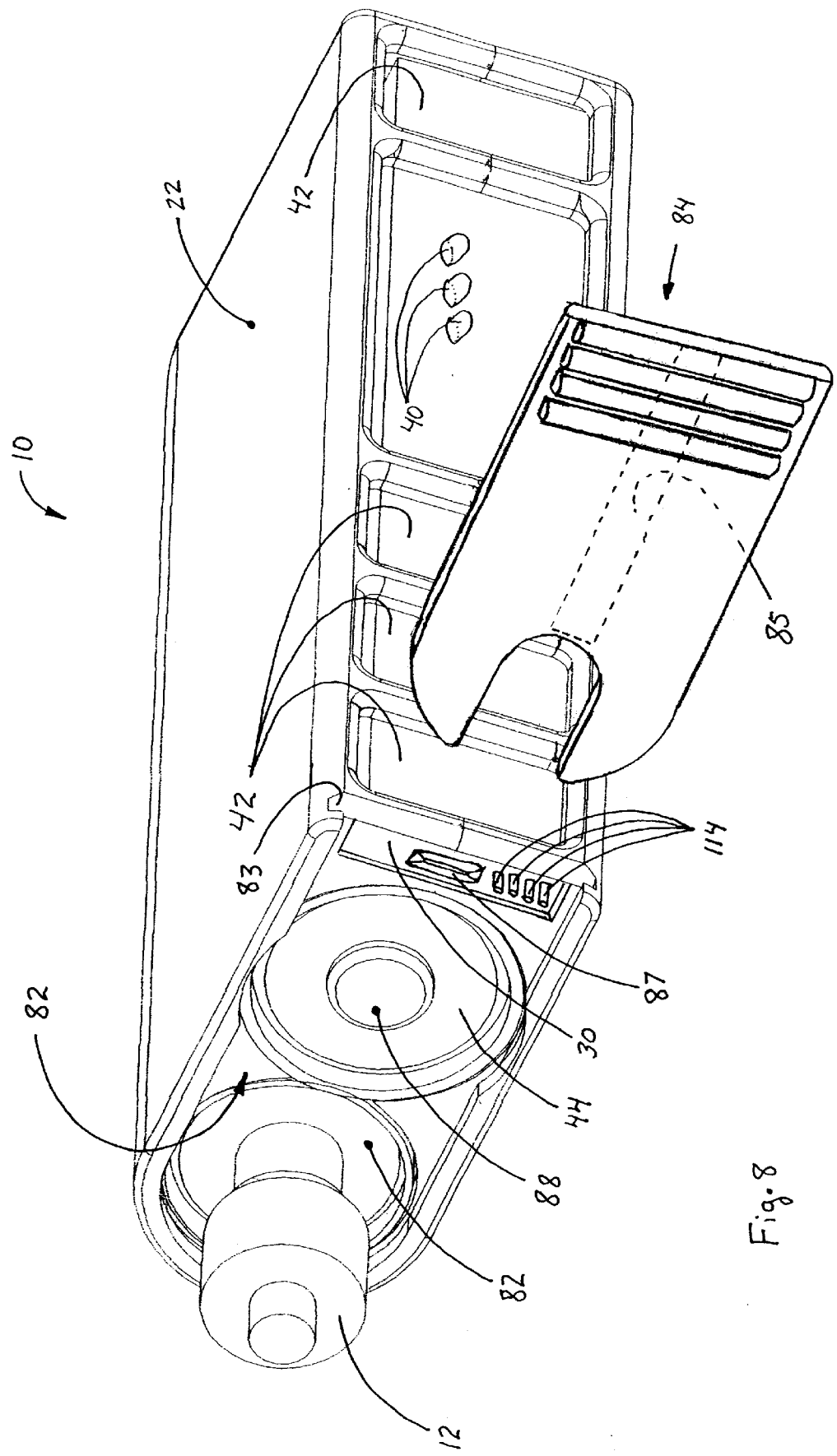
FIG. 8 is a perspective view of an infusion device with a key slid out of the housing in accordance with an embodiment of the present invention.

In preferred embodiments, the battery 44 and reservoir 12 are removable through an opening 82 in the housing 22, and the opening 82 may be closed by sliding a key 84 into a slot 83 formed in the housing 22 so that the key 84 covers the battery 44 and slides over the shoulder 86 of the reservoir 12, as shown in FIGS. 8, and 10. In this embodiment, the key 84 may be slid part way out of the slot 83 of the housing 22 to a detent position that provides a sufficient opening to remove the reservoir 12 from the housing 22 while retaining the battery 44 in place within the housing 22. The battery 44 and the reservoir 12 may both be removed from the housing 22 by entirely removing the key 84 from the slot 83 to fully expose the opening 82. In alternative embodiments, two different sliding keys (not shown) are used, one to slide over the battery 44 and another to slide over the shoulder 86 of the reservoir 12.

In preferred embodiments, the key 84 has a conductive trace 85 that connects a battery terminal 88 of the battery 44 to a power lead 87 on the electronics module 30 (see FIG. 8).

Alternatively, the entire back of the key 84 could be conductive. Therefore, if the key 84 is removed, battery power is removed from the electronics system 16. In preferred embodiments, a capacitor, or other charge storage device, maintains electrical power for at least 15 seconds and up to 3 minutes after the battery 44 is disconnected from the electronics system 16. This allows an individual time to replace the battery 44 without losing electrically stored information in the electronics system 16. In alternative embodiments, a commonly known DC converter is used to convert AC wall current into the appropriate DC current and a DC jack is plugged into the infusion device 10 to keep the infusion device 10 powered whenever battery power is low or the battery 44 is removed. In additional embodiments, the battery 44 is rechargeable by supplying a DC current to the infusion device 10 such as by plugging in a DC converter. Alternatively, the infusion device 10 may be placed on a cradle to recharge the battery 44 using induction, solar cells, or use other methods of supplying current to a battery. In additional alternatives the infusion device 10 may be powered directly using solar cells, a DC power supply such as an exterior battery or a DC converter plugged into an AC outlet, and the like.

In preferred embodiments, a switch 89 (shown in FIGS. 4, 5 and 10) is located in the housing 22 so that when the reservoir 12 is inserted far enough into the housing 22, an end of the reservoir 12 contacts the switch 89 causing the switch 89 to toggle. The switch 89 is also spring loaded to return to its original position when the reservoir 12 is removed. Thus, the switch 89 detects when the reservoir 12 is removed from the housing 22. In alternative embodiments, the infusion device 10 may include an optical reader that optically detects when a reservoir is present. In preferred embodiments, when the reservoir 12 is removed from the housing 22, the motor/gear box 48 is automatically triggered to run in reverse to fully retract the piston 56 in preparation for a new reservoir 12 to be installed. In alternative embodiments, the motor/gear box 48 retracts the piston 56 when the key 84 is removed far enough to permit removal of the reservoir 12.

In preferred embodiments, the infusion device 10 is disabled by the electronics system 16 when a predetermined usage life is expired. For instance, the electronics system 16 keeps track of the number of times the reservoir 12 is replaced and compares that number to a specified number that is programmed into a software program in the electronics system 16. Thus, the electronics system 16 will shut down the infusion device 10, stopping the flow of fluid, after the reservoir 12 is replaced a specified number of times. In preferred embodiments, the predetermined life of the infusion device 10 is expired when the reservoir 12 has been replaced sixty times. In alternative embodiments, the number of times that the reservoir 12 may be replaced before the predetermined life of the infusion device 10 is expired may be as many as one hundred and fifty times or as few as twenty times due to the durability of the components that might wear, how carefully individuals handle the infusion device 10, the types of climates the infusion device 10 is subjected to, or the like. In additional alternative embodiments, other measurements are used to detect when the infusion device's predetermined life is expired such as, the number of days of use, the number of times the battery 44 is replaced, an increase in the amount of battery power consumed to empty a reservoir 12, the number of times a key 84 is removed from the infusion device 10, or the like.

In preferred embodiments, the infusion device 10 may be refurbished and returned to the user to be used again after the electronics system 16 has disabled the infusion device 10 due to exceeding its predetermined life. In particular embodiments, the infusion device 10 can be refurbished at least once before its total life is expired. In particular embodiments, the predetermined life may increase or decrease after refurbishing due to a change in the quality of a replacement part, a new lubrication method, new information about the durability of the infusion device 10, how well the user cares for the particular infusion device, or the like. In alternative embodiments, the infusion device 10 is not refurbishable. In other alternative embodiments, the infusion device 10 may be refurbished at least 2 times and up to an indefinite number of times before its total life is expired and it can no longer be used. In particular embodiments, measurements are taken to determine if the total life of the infusion device 10 has expired such as, a significant physical shock detected by an accelerometer (perhaps a shock greater than 2.5 gs, depending on the amount of shock the infusion device 10 can handle), an increase in the amount of battery power consumed to empty a reservoir 12, a maximum temperature such as 120 degrees F. has been exceeded, the reservoir has been replaced too many times (such as 1,000 times), or the like.

In preferred embodiments, the electronics system 16 stores the control parameters, and default control parameters are programmed into the electronics system 16 during manufacturing. Preferably, the control parameters may be changed by an individual using the control system 18. In preferred embodiments, the control system 18 of the infusion device 10 has buttons 42 accessible through the housing 22. In particular embodiments, a button 42 is used to command a bolus. In other particular embodiments, additional buttons 42 may provide additional control features such as to undo a previous command, confirm a command, activate a function, initialize a software program, initialize a new reservoir 12, reset one or more control parameters to a default value, modify a control parameter, withdraw the piston 56, or the like. In preferred embodiments, LEDs indicate that control parameters have been modified by turning on or off, flashing, changing color, sequencing, or the like, In alternative embodiments, the electronics system includes a LCD, LED display, or other displays to show the status of control parameters and/or indicate to the user which control parameters are being modified. In other alternative embodiments, other feedback methods such as sounds, vibrations, or the like are used to indicate the status of control parameters.

In other embodiments, a supplemental device 90 is used as, or is used in addition to, the control system 18 to adjust, change, modify, program, input, or the like, one or all of the control parameters. The supplemental device 90 interfaces with the electronics system 16 as shown in FIG. 1. Preferably, the supplemental device 90 includes a display 98, an input system 100 and a communication system 102 that interfaces with the infusion device 10. The communication system 102 provides an initiating signal to the infusion device 10 to cause the control system 18 to go into a programming mode. Alternatively, no initiating signal is needed. Preferably the communication system 102 provides 2-way communication between the supplemental device 90 and the infusion device 10, as shown in FIG. 1. Alternatively the communication system 102 may be one way.

Figure 9:
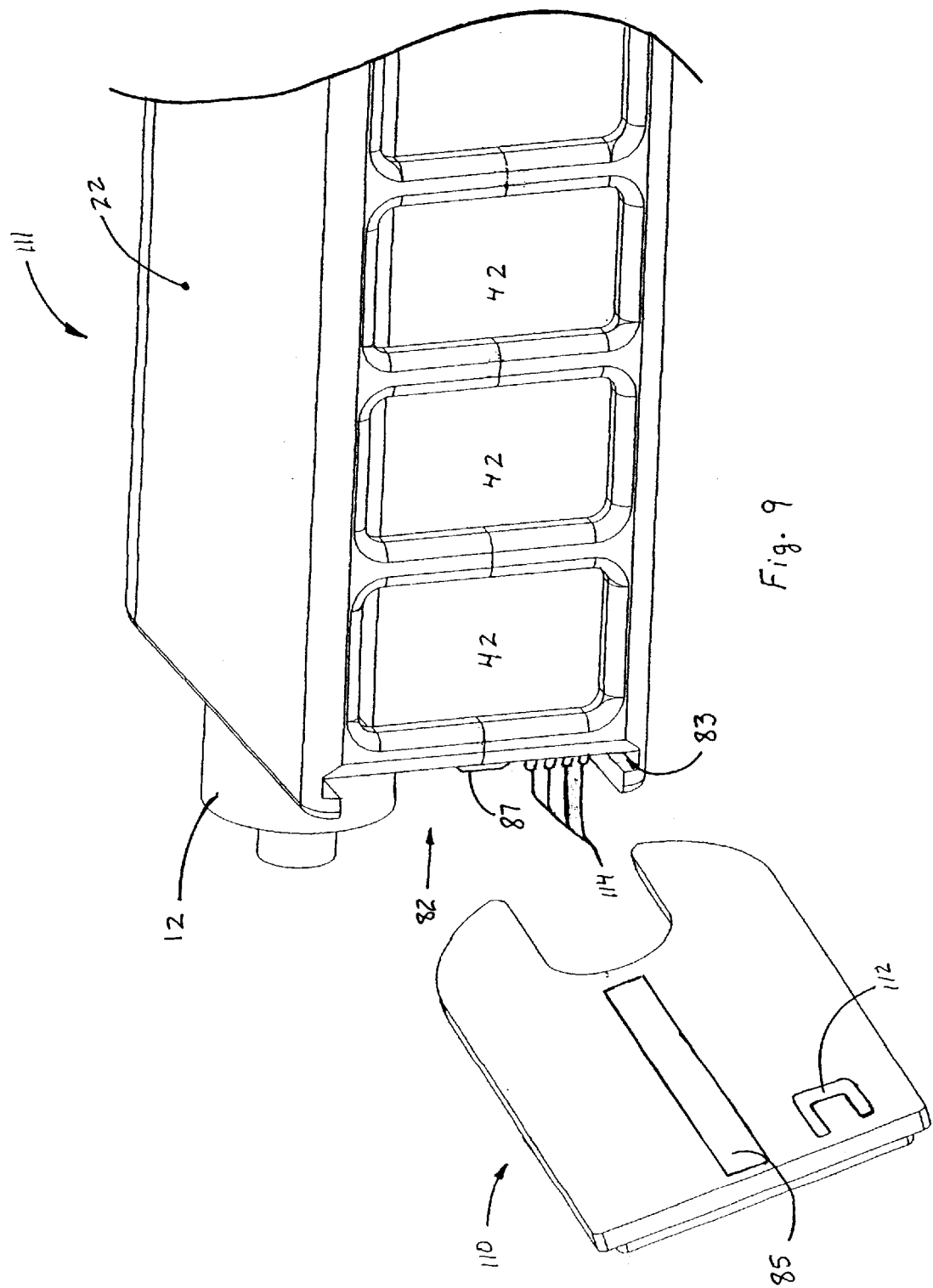
FIG. 9 is a partial perspective view of an infusion device with a key that has electrical traces in accordance with another embodiment of the present invention.
Figure 11:
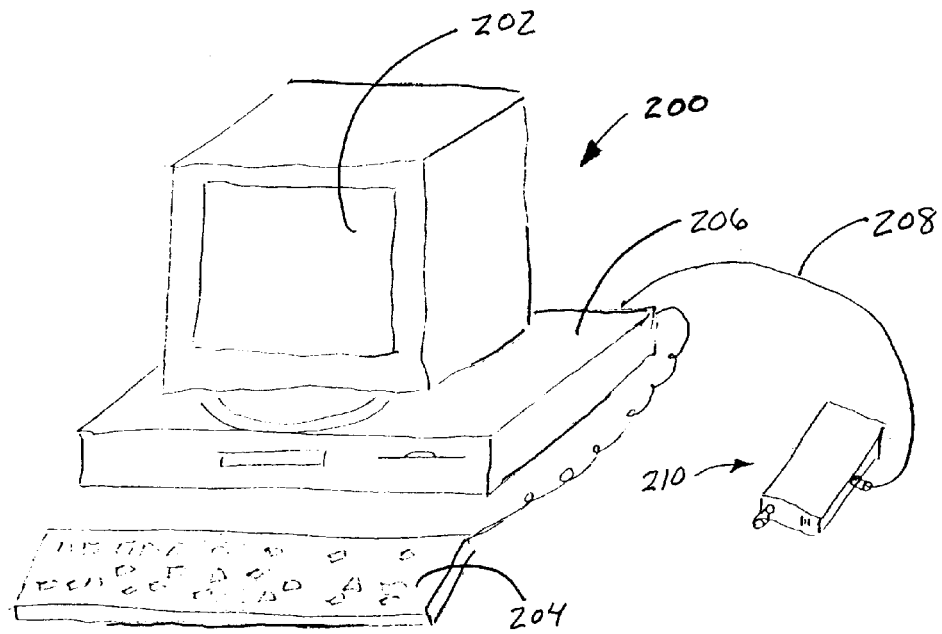
FIG. 11 is a perspective diagram of an infusion device connected to a computer in accordance with an embodiment of the present invention.
Figure 12:
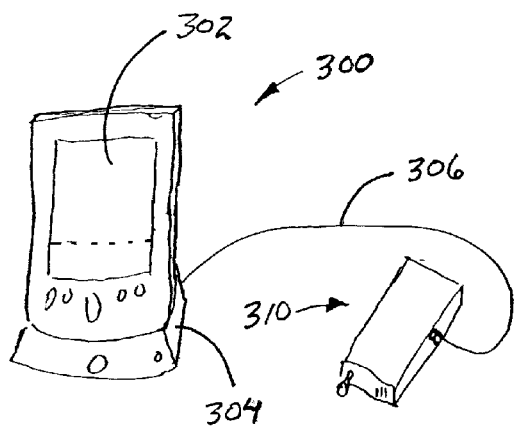
FIG. 12 is a perspective diagram of an infusion device connected to a personal digital assistant in accordance with an embodiment of the present invention.
Figure 13:
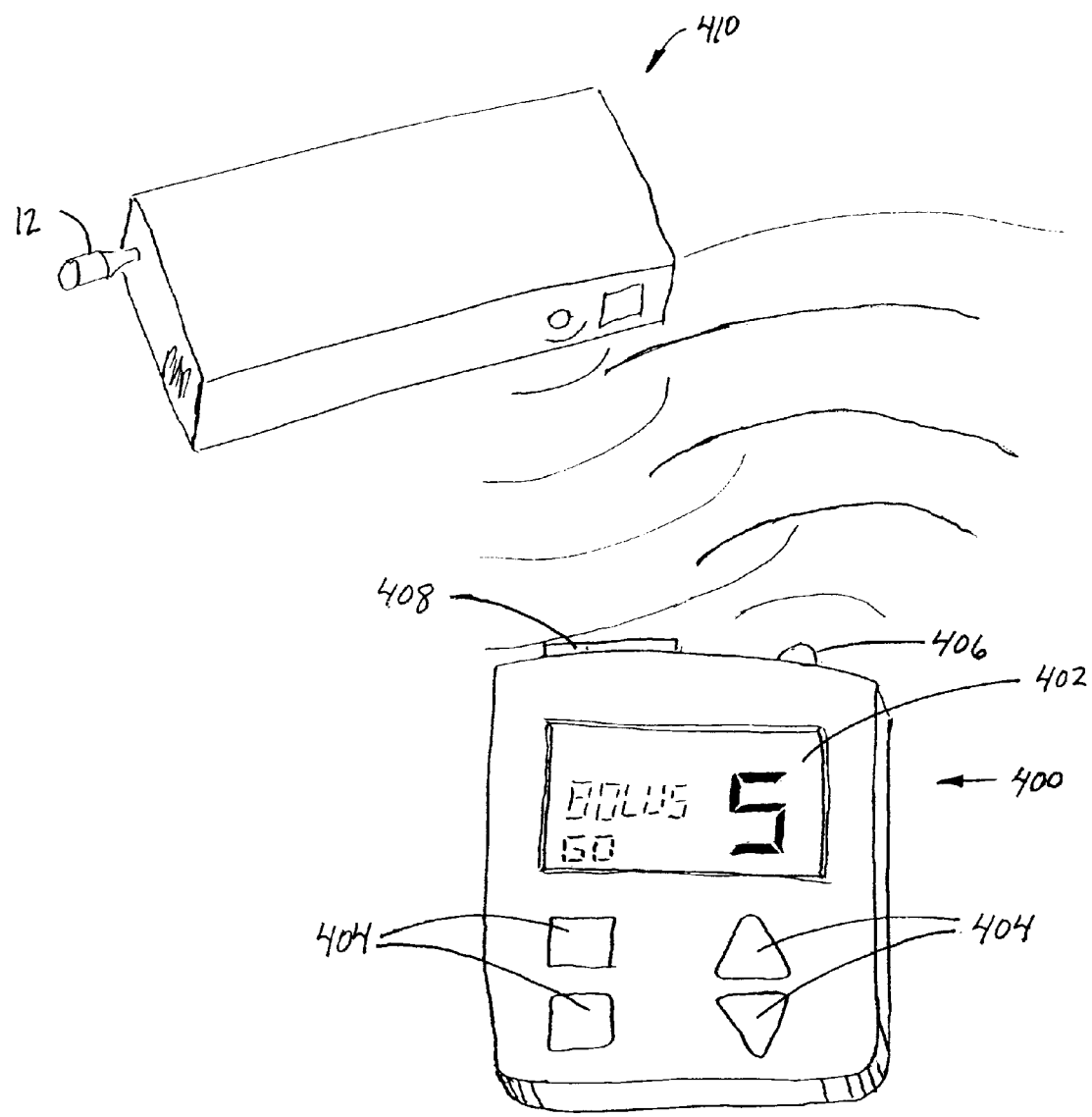
FIG. 13 is a perspective diagram of an infusion device communicating with a dedicated programming device in accordance with an embodiment of the present invention.
Figure 19A:
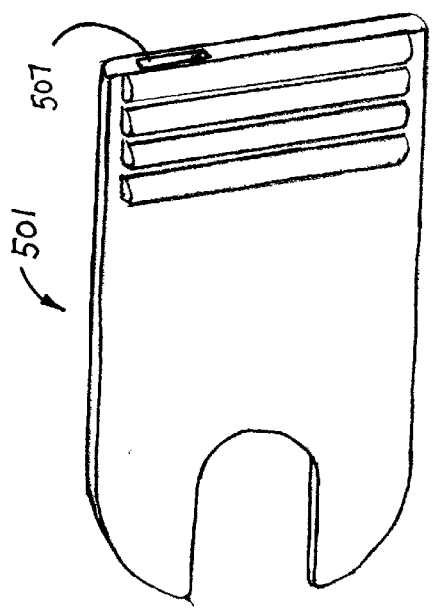
FIG. 19(a) is a perspective view of a communication key with a slot to accept a connector in accordance with an embodiment of the present invention.
Figure 19B:
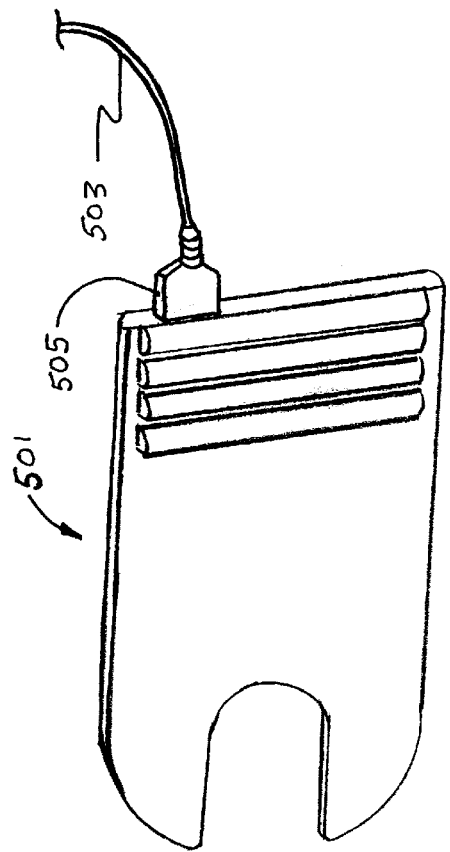
FIG. 19(b) is a perspective view of a communication key with a connector and wire attached in accordance with an embodiment of the present invention.

In particular embodiments, the supplemental device 90 is a computer system 200 that communicates with an infusion device 210. The computer system 200 has a monitor 202 as the display, a key board 204 as the input system, and the computer 206 and wires 208 as the communication system, as shown in FIG. 11. In preferred embodiments, the wires 208 are detachable at the infusion device 210. In alternative embodiments, the wires 503 carry information between the supplemental device 90 to a communication key 501, shown in FIGS. 19(a) and 19(b). The wires 503 connect to the communication key 501 through a connector 505 that mates with slot 507 in the key 501. The communication key 501 carries the information signals through electrical traces (not shown) to electrical terminals 114 on the infusion device, such as shown in FIG. 9. In particular embodiments, the wires 503 are detachable from the communication key 501 as shown in FIGS. 19(a) and 19(b). In other embodiments, the wires 503 do not detach from the communication key. In further embodiments, the supplemental device 90 is a personal digital assistant (PDA) 300 or a hand held computer such as a Palm Pilot that communicates with an infusion device 310. The PDA 300 has a touch screen LCD 302 that performs the duties of both the display and the input system, while the cradle 304 and wire 306 serve as the communication system, as shown in FIG. 12. In still further embodiments, the PDA may communicate using a wireless connection, such as by IR, RF, or the like. In still other embodiments, the supplemental device 90 is a dedicated programming device 400, that communicates with an infusion device 410 as shown in FIG. 13. The dedicated programming device 400 has a LCD 402 for its display, buttons 404 as the input system and a radio transmitter 406 and receiver 408 as the communication system.

In alternative embodiments, the communication system 102 in the supplemental device 90 uses IR signals, optical signals, direct electrical contact, laser signals, combinations of carrier frequencies, or the like. In further alternative embodiments, the display 98 is monitor, a touch screen, LEDs, lights, or the like. In more alternative embodiments, the input system 100 includes a keyboard, a button, a touch screen, a touch pad, a dial, a switch, a microphone, a joystick, a computer mouse, a roller ball, or the like.

Figure 20:
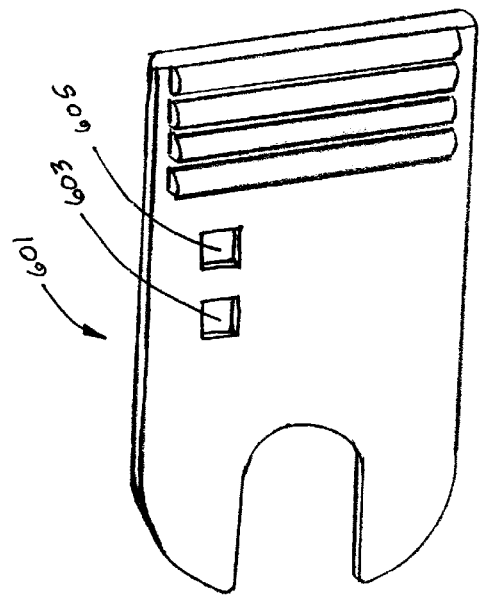
FIG. 20 is a perspective view of a communication key for RF communication in accordance with an embodiment of the present invention.
Figure 21:
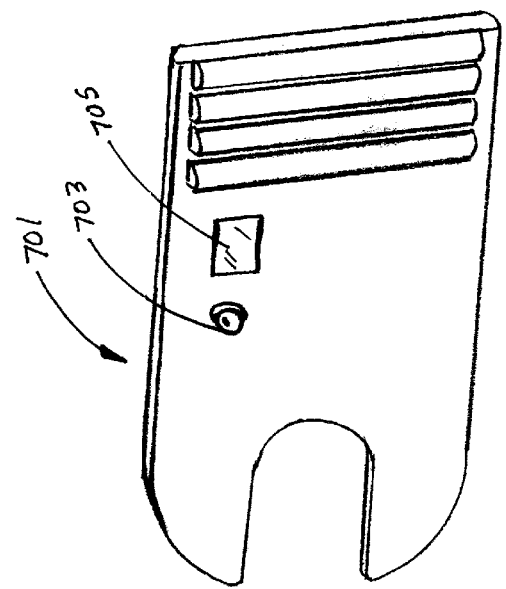
FIG. 21 is a perspective view of a communication key for IR communication in accordance with an embodiment of the present invention.

In particular alternative embodiments, a communication key is used that includes portions of the communication system. For example, a communication key 601 has a radio frequency transmitter 603 and receiver 605, shown in FIG. 20. Alternatively, a communication key 701 has a infra red transmitter 703 and receiver 705, shown in FIG. 21. Other communication devices may be included in the communication key that use other carriers such as, ultrasonic, visual light, video frequencies, ultra violet, laser, microwave, or the like. In alternative embodiments, installation of the communication key into the infusion device causes the control system of the infusion device to go into a programming mode. In particular alternative embodiments, the infusion device enters a programming mode when the communication key contacts a switch (not shown), contacts electrical terminals 114, is detected by a sensor such as an optical or magnetic proximity sensor, pushes a button, or the like.

Figure 14:
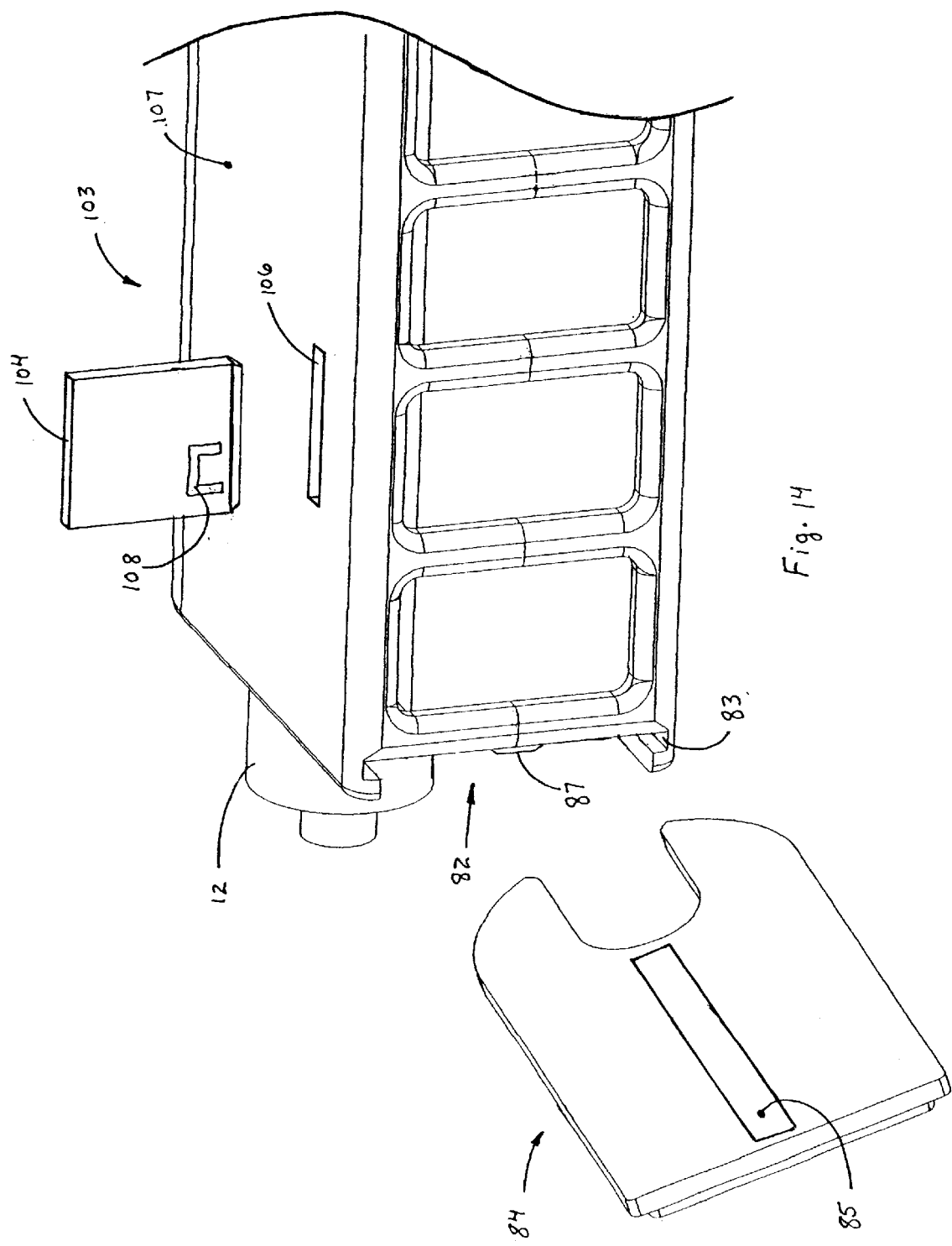
FIG. 14 is a partial perspective view of an infusion device with a tab that has electrical traces in accordance with a further embodiment of the present invention.
Figure 15:
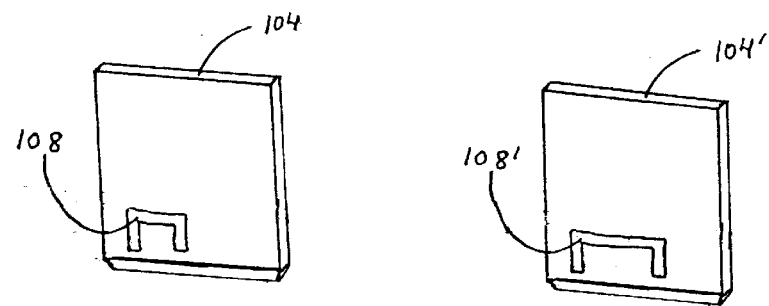
FIG. 15 is a perspective view of two tabs with different electrical traces in accordance with an embodiment of the present invention.

In another embodiment, control parameters such as the basal and/or bolus levels, maximum or minimum basal rate or the like, are set in an infusion device 103 when a tab 104, with at least one conductive trace 108, is inserted into a slot 106 on the housing 107, such as shown in FIG. 14. The conductive trace 108 establishes connections between some of the electrical terminals (not shown) in the infusion device 103. Different patterns of conductive traces 108 and 108' on different tabs 104 and 104' (shown as examples in FIG. 15) connect different electrical terminals (not shown) in the infusion device 103. As different electric terminals (not shown) are connected to each other, different control parameters, such as basal rates, are set and then used by the electronics system 16. The number of electrical terminals (not shown) and the number of conductive traces 108 may vary depending on the number of control parameters that are controlled using the tabs 104. The number of different patterns of unique conductive traces 108, and therefore different tabs 104, is dependent on the number of control parameters that are controlled with the tabs 104 and the number of variations needed for each command parameter. As an example of an application using tabs 104 to control the infusion device 103, a doctor may prescribe a particular basal rate and therefore insert a particular tab 104 into the infusion device 103. Later, if a patient's needs have changed, the doctor may remove the originally prescribed tab 104 and insert a different tab 104 that causes the infusion device 103 to dispense the fluid at a different rate. In alternative embodiments, the tabs may include an optical pattern that is read by an optical reader in the housing. For instance, the optical pattern may be similar to that shown in FIG. 15. Alternatively, other patterns or a bar codes may be used. In further alternative embodiments, the tabs may include information stored on a magnetic media. And the information may be read by a magnetic reader contained within the housing.

In alternative embodiments, the tab is in the form of a tab/key 110 that slides into slot 83 on an infusion device 111 to hold the battery 44 and/or reservoir 12 in place as shown in FIG. 9.

Figure 16:
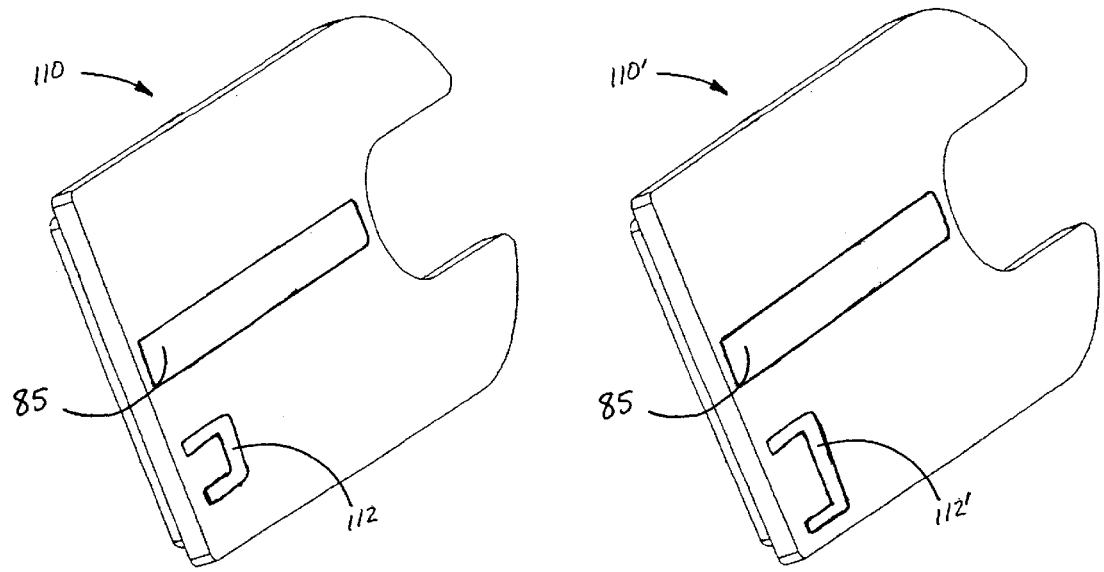
FIG. 16 is a perspective view of two keys with different electrical traces in accordance with an embodiment of the present invention.

Conductive traces 112 on the tab/key 110 establish connections between some of electrical terminals 114. Different patterns of conductive traces 112 and 112' on different tab/keys 110 and 110' (shown as examples in FIG. 16) connect different electrical terminals 114. Again, as different electrical terminals 114 are connected to each other, different control parameters such as basal rates, or the like, are set and used by the electronics system 16.

Figure 17:
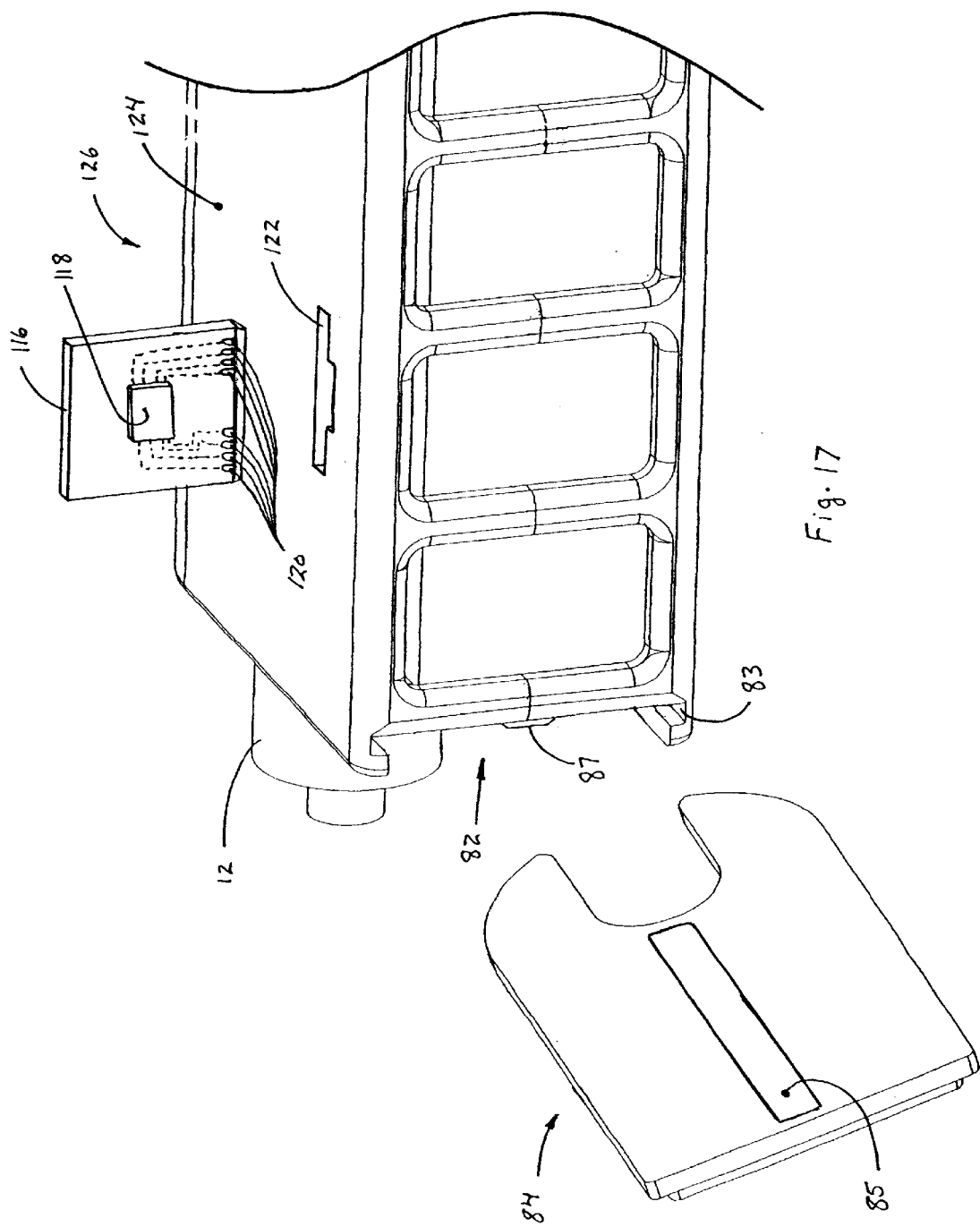
FIG. 17 is a partial perspective view of an infusion device with a tab that has a programmable chip in accordance with an embodiment of the present invention.

In other embodiments, a tab 116 has a programmable chip 118, such as shown in FIG. 17, that is programmed with different control parameters before insertion into a slot 122 in a housing 124 of a infusion device 126. One or more conductive traces 120 on the tab 116 connect the chip 118 to the electronics system 16 through electrical terminals (not shown) in the housing 124. In particular embodiments, different tabs 116 have chips 118 that are programmed with different basal rates. Therefore, to change the basal rate for an infusion device 10, an individual may remove the existing tab 116 from the housing 124 and install a different tab 116 that includes a chip 118 that is programmed to command a different basal rate. In particular embodiments, the tabs 116 are removed from the infusion device 126, and the chips 118 are re-programmed with different control parameters, and then the tab 116 is re-installed into the infusion device 126. In alternative embodiments, the chips 118 are not re-programmable, and a new tab 116 with a new chip 118 is used when control parameters must be changed.

Figure 18:
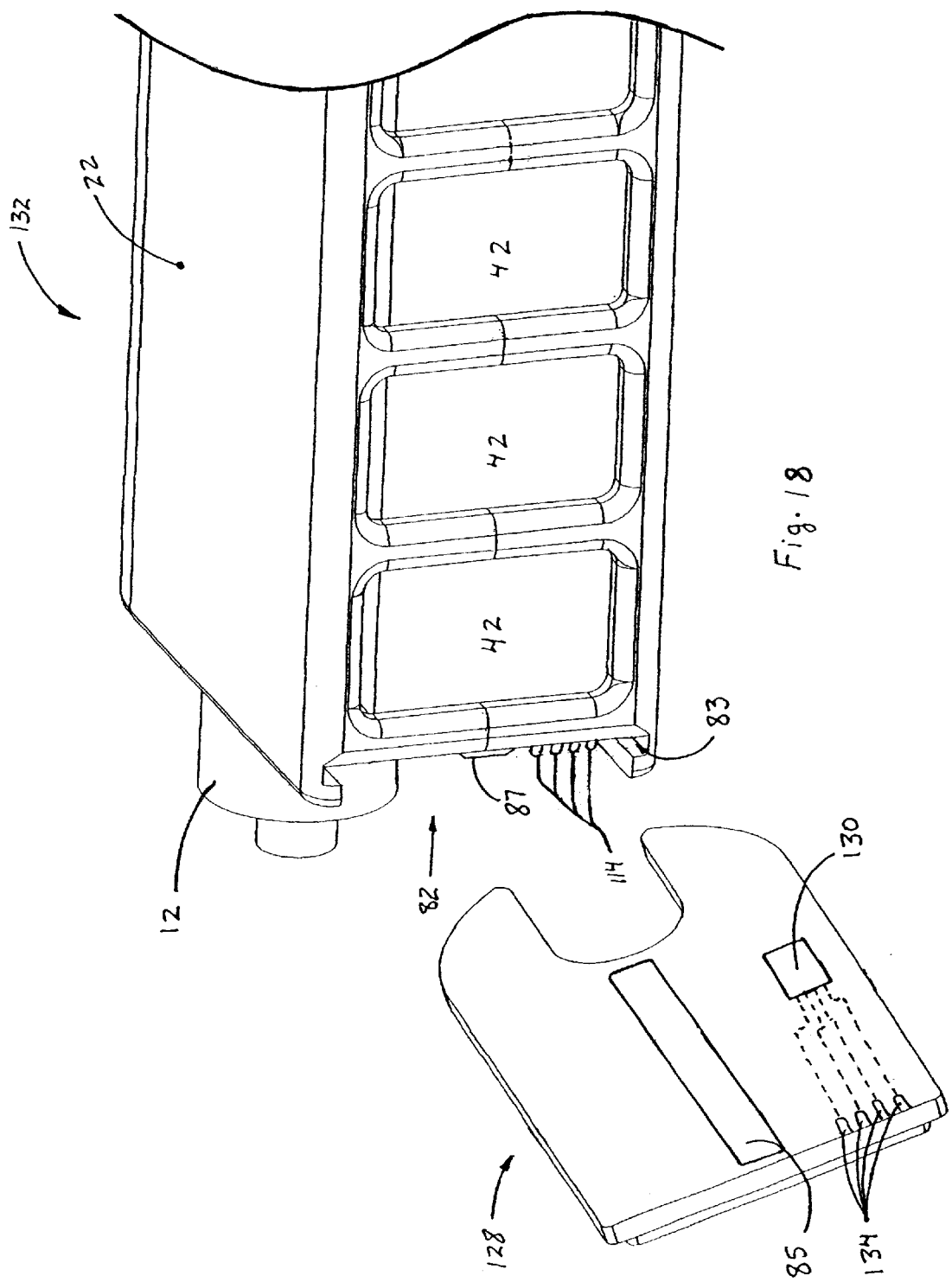
FIG. 18 is a partial perspective view of an infusion device with a key that is that has a programmable chip in accordance with an embodiment of the present invention.

In alternative embodiments, the tab is in the form of a tab/key 128 and has a programmable chip 130 such as shown in FIG. 18, that is programmed with different control parameters before insertion into slot 83 of the housing 22 of infusion device 132. One or more conductive traces 134 on the tab/key 128 connect the chip 130 to the electronics system 16 through electrical terminals 114.

In additional alternative embodiments, a tab/key, normally used to establish control parameters as described above, may be a communication key. The communication key enables the infusion device to communicate with a supplemental device 90 to change control parameters or transfer data. In particular embodiments, a tab/key that is not a communication key is reinserted into the infusion device for normal operation after the communication key has completed the communication with the supplemental device 90. In other particular embodiments, the communication key is left in the infusion device or a different tab/key is used after the communication device is removed.

In other particular embodiments, the tab/key includes communication devices. For example, a tab/key with a computer chip (such as tab/key 128 described above) may include a slot to accept a connector such as communication key 501 shown in FIGS. 19(a) and 19(b). Other communication devices such as IR, RF, ultrasonic, or the like may be included on a tab/key. In particular embodiments, the supplemental device 90 can reprogram computer chips included on the tab/key. In alternative embodiments, a communication device is included on a tab that does not serve as the key that covers the battery 44 and the reservoir 12.

In preferred embodiments, the tabs are color coded to identify the basal rate, or other control parameters, they are programmed to command. In alternative embodiments, other identification methods may be used to indicate the basal rate, and/or other control parameters, associated with a particular tab such as, a code number, a serial number, a lot number, a batch number, a name, or the like. Methods of applying the identification include, stamping, silkscreening, printing, typing, labels, embossing, imprinting, molding, or the like. In additional alternative embodiments, other means are used to identify tabs that have different control parameters from each other such as, surface textures, flexibility, materials, a raised patterns, printed patterns, or the like.

Tabs may be used to modify characteristics of other infusion devices as well, such as those described in U.S. Pat. Nos. 4,562,751; 4,685,903; 5,080,653; 5,505,709; 5,785,688; 5,814,020 and 5,097,122; and disclosed in U.S. patent applications Ser. No. 09/334,858, filed Jun. 17, 1999 and entitled "Infusion Pump With Remote Programming and Carbohydrate Calculator Capabilities", and Ser. No. 09/429,352, filed Oct. 28, 1999 and entitled "Compact Pump Drive System", which are hereby incorporated by reference. Tabs may also be used to calibrate or control various features of characteristic or analyte monitor systems such as those described in U.S. patent applications Ser. No. 09/465,715, filed Dec. 17, 1999 and entitled "Telemetered Characteristic Monitor System And Method Of Using The Same"; and Ser. No. 09/246,661, filed Feb. 5, 1999 and entitled "An Analyte Sensor And Holter-Type Monitor System And Method Of Using The Same"; and also Ser. No. 09/334,996, filed Jun. 17, 1999 and entitled "Characteristic Monitor With A Characteristic Meter And Method Of Using The Same", which are all hereby incorporated by reference herein.

In preferred embodiments, substantially all parts of the infusion device 10 are designed to slide or snap together during assembly. In particular embodiments, no screws are used on the infusion device 10. In preferred embodiments, the housing 22 is plastic and is sealed using ultrasonic fusing. In alternative embodiments, other methods are used to seal the housing 22 such as gluing, bonding, fusing, melting, snapping, pressing, or the like. In other alternative embodiments, the housing 22 is made of other materials such as metal, rubber, resin, foam, or the like. Refurbishing of the infusion pump 10 may require destruction of the housing 22.

While the description above refers to particular embodiments of the present invention, it will be understood that many modifications may be made without departing from the spirit thereof The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A reusable external infusion device with a predetermined usage life for infusing a fluid into a body, the infusion device comprising:
    a housing;
    a replaceable reservoir receivable in the housing that contains the fluid before infusing, wherein the replaceable reservoir has a usage life substantially shorter than the predetermined usage life of the infusion device;
    a power supply contained in the housing;
    a drive system coupled to the power supply and that forces fluid from the reservoir; and
    an electronics system coupled to the power supply and the drive system and that regulates the power from the power supply to the drive system;
    wherein after the infusion device's predetermined usage life has expired, the infusion device may be refurbished at least once to function for another predetermined usage life.

2. A reusable external infusion device for infusing a fluid into an individual, the reusable external infusion device comprising:
    a housing;
    a replaceable reservoir that is inserted into the housing and that contains the fluid; and
    a drive system that forces the fluid from the reservoir,
    wherein the housing of the reusable external infusion device accepts a key that includes a communication device for communicating between the reusable external infusion device and a supplemental device.

3. A reusable external infusion device for infusing a fluid into an individual, the reusable external infusion device comprising:
    a housing;
    replaceable reservoir that is inserted into the housing and that contains the fluid;
    a drive system that forces the fluid from the reservoir;
    a power supply contained in the housing; and
    an electronics system coupled to the power supply and the drive system that regulates the power from the power supply to the drive system and controls the external infusion device in accordance with one or more control parameters,
    wherein the housing of the reusable external infusion device includes an opening to accept a tab that includes a communication device for communicating between the reusable external infusion device and a supplemental device to adjust one of the one or more control parameters of the external infusion device.

4. A reusable external infusion device for infusing a fluid into an individual, the reusable external infusion device comprising:
    a housing;
    a replaceable reservoir that is inserted into the housing and that contains the fluid;
    a drive system that forces the fluid from the reservoir;
    a power supply contained in the housing; and
    an electronics system coupled to the power supply and the drive system that regulates the power from the power supply to the drive system and controls the external infusion device in accordance with one or more control parameters
    wherein the housing of the reusable external infusion device includes an opening to accept a tab/key that includes a communication device for communicating between the reusable external infusion device and a supplemental device to adjust one of the one or more control parameters of the external infusion device.

5. A reusable external infusion device for infusing a fluid into an individual, the reusable external infusion device comprising:
    a housing; and
    a replaceable reservoir that is inserted into the housing and that contains the fluid,
    wherein the housing includes an opening to insert a removable tab that includes a programmable chip that contains at least one control parameter to control the reusable external infusion device.

6. A reusable external infusion device for infusing a fluid into an individual, the reusable external infusion device comprising:

a housing; and a replaceable reservoir that is inserted into the housing and that contains the fluid, wherein the housing includes an opening to receive a tab that includes at least one conductive trace that establishes electrical contact between at least one set of electrical terminals inside the housing to set one or more control parameters of the reusable external infusion device based on the electrical terminals connected inside the housing.

7. A reusable external infusion device according to claim 6, wherein the housing is adapted to receive at least one of at least two different tabs that are insertable into the housing, and the at least two different tabs each have different electrical jumper configurations that establish electrical contact between different electrical terminals inside the housing, and wherein connecting different electrical terminals causes the external infusion device to dispense fluid at different rates.

8. A reusable external infusion device for infusing a fluid into an individual, the reusable external infusion device comprising:

a housing; and a replaceable reservoir that is inserted into the housing and that contains the fluid, wherein the housing includes an opening adapted to receive at least one tab with an optically readable pattern, and wherein the housing includes an optical reader to read the optically readable pattern on the at least one tab to control at least one control parameter of the reusable external infusion device.

9. A reusable external infusion device for infusing a fluid into an individual, the reusable external infusion device comprising:

a housing; and a replaceable reservoir that is inserted into the housing and that contains the fluid, wherein the housing includes an opening adapted to receive at least one tab that includes magnetically stored information and wherein the housing includes a magnetic reader to read the magnetically stored information from the at least one tab to control at least one control parameter of the reusable external infusion device.

* * * * *